(12) United States Patent
Aastrup et al.

(10) Patent No.: US 8,591,812 B2
(45) Date of Patent: Nov. 26, 2013

(54) PIEZOELECTRIC SENSOR ARRANGEMENT

(75) Inventors: Teodor Aastrup, Stockholm (SE); Jan Smith, Stockholm (SE); Henrik Anderson, Sundbyberg (SE)

(73) Assignee: Attana (SE)

( * ) Notice: Subject to any disclaimer, the term of this patent is extended or adjusted under 35 U.S.C. 154(b) by 1809 days.

(21) Appl. No.: 10/539,065

(22) PCT Filed: Dec. 18, 2003

(86) PCT No.: PCT/SE03/02001
§ 371 (c)(1),
(2), (4) Date: Jun. 15, 2005

(87) PCT Pub. No.: WO2004/057319
PCT Pub. Date: Jul. 8, 2004

(65) Prior Publication Data
US 2006/0141608 A1  Jun. 29, 2006

(30) Foreign Application Priority Data
Dec. 19, 2002 (SE) ........................ 0203772

(51) Int. Cl.
*G01N 11/16* (2006.01)
(52) U.S. Cl.
USPC .............. 422/68.1; 435/287.1; 73/61.79
(58) Field of Classification Search
USPC .............. 422/68.1; 435/287.1; 73/61.79
See application file for complete search history.

(56) References Cited

U.S. PATENT DOCUMENTS

| | | | |
|---|---|---|---|
| 4,548,514 A * | 10/1985 | Ganter | 368/291 |
| 4,569,438 A * | 2/1986 | Sheffler | 206/37 |
| 4,974,952 A * | 12/1990 | Focht | 359/398 |
| 5,321,331 A * | 6/1994 | Baer et al. | 310/313 D |
| 5,922,604 A * | 7/1999 | Stapleton et al. | 436/46 |
| 5,992,215 A * | 11/1999 | Caron et al. | 73/24.01 |
| 6,029,500 A * | 2/2000 | Tom | 73/31.05 |
| 6,196,059 B1 | 3/2001 | Fraunhofer | |
| 2002/0023409 A1 * | 2/2002 | Py | 53/426 |

FOREIGN PATENT DOCUMENTS

| | | |
|---|---|---|
| DE | 197 34 708 C1 | 3/1999 |
| EP | 0 453 820 B1 | 10/1991 |
| GB | 2 154 058 A | 8/1985 |
| WO | 0212873 A2 | 2/2002 |

OTHER PUBLICATIONS

Másson et al.; (Jul. 1, 2995) "Quartz Crystal Microbalance Bioaffinity Sensor for Biotin"; Source: Analytical Chemistry, vol. 67, No. 13, pp. 222-225.

(Continued)

*Primary Examiner* — Paul Hyun
(74) *Attorney, Agent, or Firm* — Banner & Witcoff, Ltd.

(57) ABSTRACT

A piezoelectric sensor arrangement for analysis of fluid samples includes a signal source, a measuring device and a docking system. The sensor arrangement comprises a first part capable of receiving a sensor element that exposes a piezoelectric quartz crystal, a second part comprising fluid channels for the sample and a flow cell element, which preferably is removable and which comprises a recess, and inlet and outlet fluid channels for leading a fluid through the recess. The first and second parts are movable in relation to each other between a closed position and an open position and are arranged such that in the closed position the recess of the flow cell element is sealingly covered by the piezoelectric quartz crystal so that a flow cell is formed by the flow cell element and the quartz crystal.

23 Claims, 6 Drawing Sheets

(56) References Cited

OTHER PUBLICATIONS

Shana et al.; (1990) "Theory and application of a quartz resonator as a sensor for viscous liquids"; Source: Analytica Chimica Acta, 231, pp. 317-320.

Stevenson et al.; (2001) "Gigahertz surface acoustic wave probe for chemical analysis"; Source: Analyst, 126, pp. 1619-1624.

Thompson et al.; (Mar. 1987) "The Potential of the Bulk Acoustic Wave Device as a Liquid-Phase Immunosensor"; Source: IEEE Transactions on Ultrasonics, Ferroelectrics, and Frequency Control, vol. UFFC-34, No. 2, pp. 127-135.

* cited by examiner

PIEZOELECTRIC SENSOR ARRANGEMENT

CROSS REFERENCE TO RELATED APPLICATIONS

This application is a national stage application of International Application PCT/SE03/02001, filed Dec. 18, 2003, designating the United States of America, which claims the benefit of Swedish Patent Application No. 0203772-9, filed Dec. 19, 2002.

TECHNICAL FIELD

The present invention relates to a piezoelectric sensor arrangement, a sensor element and a flow cell element to be used in the sensor arrangement.

BACKGROUND

A Quartz Crystal Microbalance (QCM) system utilizes the piezoelectric effect of a quartz crystal. In such a system a quartz crystal that is placed between two electrodes, which are connected to an AC-potential, begins to oscillate if the frequency of the AC-potential is close to the resonance frequency of the oscillation mode for the quartz crystal. The resonance frequency of the quartz crystal is a function of many parameters, such as temperature, pressure, cut angel of the crystal, mechanical stress and thickness of the crystal. The resonance frequency is inversely proportional to the square root of the thickness of the crystal as described by the Saurbrey equation:

$$\Delta f = -\frac{2f^2}{\rho v}\frac{\Delta m}{A}$$

where f is the resonance frequency, ρ the density of quartz, v the shear wave velocity in quartz, A the electrode area and Δm the sample mass. Typical resonance frequencies used in liquid applications range from 1 MHz to 50 MHz. The crystal is normally AT-cut with a circular or quadratic shape with a diameter of approximately 5-10 mm. The electrodes are normally of gold on both sides, but other metals are not unusual. The electrodes are very thin compared to the quartz crystal plate and can therefore be considered as part of the crystal plate. When material is added to or removed from one of the electrodes, it becomes thicker or thinner, i.e. the associated weight of the electrode changes. As a consequence of the mass change of the electrode, the resonance frequency of the crystal plate will either decrease or increase and hence the change of resonance frequency can be measured to detect the mass change of the electrode. The mass resolution of a QCM system can be as low as 1 pg/cm$^2$, corresponding to less than 1% of a monolayer of hydrogen.

A typical QCM piezoelectric system comprises a sensor unit, a sample insertion unit, a frequency counter, and signal presentation equipment and buffer and waste containers. A sample, which can contain any chemical substance of interest, is introduced into the sensor unit by the sample insertion unit. The sensor unit contains a piezoelectric resonator, a sensor chamber, flow channels to and from the chamber and an oscillating circuit. The sample induces an interaction with the piezoelectric sensor surface, which can in turn be observed by monitoring the oscillating characteristics of the crystal plate, e.g. by measuring changes in the piezoelectric resonator frequency. The resonator utilised by the sensor unit includes a crystal plate, which is a plane piezoelectric crystal. The crystal plate is provided with electric contact areas for an electrode and a counter electrode on its surface, which electrodes are connectable to a signal source (e.g. an alternating voltage source) as well as to a measurement device. For measuring, the piezoelectric crystal plate is on one side brought into contact with the liquid sample to be examined. The crystal responds to the accumulation of the mass of the substance to be detected or to a change in the physical properties of the sample by altering its resonance frequency and/or oscillation amplitude.

Piezoelectric sensors can be used for analysis of the viscosity of a liquid sample and are particularly suitable for studying chemical and biochemical interactions. If a piezoelectric sensor is to be used for the latter purpose, the electrode that is to be exposed to the sample is provided with a specific surface coating, which will interact with the sample. Such surface coated piezoelectric sensors can be used within for example surface science, biotechnology research and pharmaceuticals development. Other applications can be as sensor for detection of hazardous gases or substances such as environmental contaminants, biochemical warfare agents and illicit drugs, e.g. narcotic substances or performance improving drugs (doping). A third area for application of the technology is health diagnostics, where the sensor can be used for examining patients for different diseases by analysis of human blood or other body fluids. The use of piezoelectric resonators in these areas has up to now not gained a commercial acceptance, due to the drawbacks of the hitherto available systems.

The crystal plates utilised by piezoelectric resonators are usually small oscillator quartz crystal plates. However, due to the structure of the small plates, the resonating behaviour of the resonator may be impaired, i.e. by mechanical tension in the small plates caused by the holding carriers or by contacting with electric lines.

An example of a small oscillator quartz crystal plate that is fixed in a holding carrier is described in GB 2 154 058 A. The small oscillator quartz plate is provided with electrodes deposited on its surface and is spatially fixed between two holding clamps and electrically contacted. A disadvantage of this arrangement is that even with the least exerted force, acting on the two parts, which are spaced apart, a mechanical tension can be generated in the small plate glued between parts, thereby influencing its resonance behaviour.

As already mentioned piezoelectric resonators are advantageously used as active sensor elements, e.g. for detecting a substance in a medium, for instance, for measuring the concentration of the substance in a liquid. When working with liquids, the oscillator quartz to be electrically contacted has also to be insulated liquid-tight against the to-be-examined liquid in order to prevent electric short circuits. Such a sensor is described in EP 453 820 B1. This sensor provides a small oscillator quartz plate, which is clamped on both sides between two silicon seals and, in addition, is contacted to conductive adhesive substances. However, the use of conductive adhesives has the consequence that the electric contact cannot be disconnected, which, for instance, makes replacing the small oscillator quartz plate impossible or at least requires great manual skill. Moreover, the silicon seals surrounding the small oscillator plates on all sides have to be made with great precision in order to prevent deformations in the small plate.

These known sensors for measuring concentrations or reactions of a substance in liquids and for determining the physical properties of liquids operating on the basis of piezoelectric resonators have in brief the following drawbacks:

The small oscillator quartz plates are glued to or clamped in a holding means, which can impair the resonance behaviour of the resonator itself due to mechanical tensions. Moreover, glued and clamped electric contacts on the surface of small oscillator quartz plates are not totally reliable, in particular, when employed for measuring concentrations of substances in liquids. Precautions must be taken in order to avoid short circuits. A stable and uniform quality of the contacting is not possible by this means.

In the known cases, the piezoelectric resonators are provided with contact areas, which are to be connected to an electrical oscillation circuit and respectively to a measuring system, for electrical contacting on both its front side as well as on its rear side. The integration of the piezoelectric resonator in a casing with respective electric contacting is difficult and time consuming. Good stable quality of the electric properties, in particular, when using a piezoelectric resonator in a holding means, which permits bringing the small oscillator plate into contact with a sample to on one side, is impossible.

Holding means of this type are also called flow-through cells, which are a unit, in which the already electrically contacted small oscillator quartz plate is connected to the connecting electrodes. Furthermore, defined supply and drain channels are provided via which the sample can be selectively supplied to the piezoelectric resonator and drained again. For flow-through cells of this type, the user needs much time and manual skill in replacing the crystal. In particular, in the field of biosensors, replacement often becomes necessary, because each different substance to be detected requires a specially prepared flow-through cell. In an attempt to overcome these problems the resonator has been integrated in a flow-through cell, as described in U.S. Pat. No. 6,196,059. However, even though such an integrated flow-through cell may be easy to handle, it has to be manufactured with high precision. Another drawback is that the surface coating of the electrode area has to be performed before gluing the resonator to the flow cell and the entire flow cell must be disposed of after use. In addition, there is a risk that the gluing process may interact with the surface coating and disable the desired functionality of the surface coating.

The object of the present invention is to provide a piezoelectric sensor arrangement that gives reliable analysis results, has inexpensive disposable parts and is easy to handle.

SUMMARY OF THE INVENTION

The object of the present invention is achieved by a piezoelectric sensor arrangement in which inter-related parts interact so as to form a flow cell. The first of the inter-related parts is a sensor element, which holds a piezoelectric crystal. The second of the inter-related parts is a flow cell element, which comprises a recess through which the sample is to be led during use and an abutting part of which at least the upper portion is made of an elastic material. Both inter-related parts are designed so that, when brought together before the analysis, the recess of the flow cell element is covered by the crystal of the sensor element thus forming a flow cell. The inter-related parts are held together only by means of a pressing force, and thus no adhesives or mechanical fixing means are needed. Since at least a portion of the abutting part of the flow cell element is made of an elastic material, i.e. the surface that will come into contact with the crystal (abutting surface) and the portion of the flow cell element next to that surface, the flow cell element is capable of sealing against the crystal, without breaking it.

The present invention thus provides a piezoelectric sensor arrangement for analysis of fluid samples, which includes a signal source, a measuring device and a docking system, which arrangement comprises a first part and a second part. The second part comprises fluid channels for the sample and said first and second parts are movable in relation to each other between a closed position and an open position. Moreover, the first part is provided with means for receiving a sensor element, which exposes a piezoelectric quartz crystal having a freely accessible electrode, which is intended to come into contact with the fluid sample. This means comprises an opening through which the crystal of the sensor element can come into contact with a flow cell element. The second part comprises fluid channels for the sample and a flow cell element that comprises an abutting part, which is provided with an outwardly open recess, and inlet and outlet fluid channels for leading a fluid through the recess. The recess is surrounded by an abutting surface, and at least said abutting surface and the portion of the abutting part closest to the abutting surface is made of an elastic material, which is capable of sealing against the piezoelectric quartz crystal. The first and second parts are arranged such that when the first and second parts are moved from the open position to the closed position, the abutting surface of the abutting part of the flow cell element comes into abutment with the exposed piezoelectric quartz crystal of the sensor element whereby in the closed position the piezoelectric quartz crystal sealingly covers the recess of the flow cell element thus creating a flow cell.

In comparison to the conventional liquid connection systems, which use flow cells composed of a plurality of components, such as the one in U.S. Pat. No. 6,196,059 B1, manufacturing costs are lowered. This is an essential advantage, since the sensor crystals are made only for single use and must be disposed of after use. In addition, the sensor arrangement of the present invention is very easy to handle, since the user does not need to possess any personal skill to assemble the flow cell.

The present invention also relates to a sensor element for analysis of fluid samples in a piezoelectric sensor arrangement, which comprises a carrier to which a piezoelectric quartz crystal is attached, said crystal having a front side and a rear side, where said front side is intended to come into contact with the fluid sample and is provided with a front electrode and said rear side is provided with a rear electrode, both electrodes being adapted to receive electric signals for generation of an oscillating motion of the crystal, which crystal is arranged on the carrier in such a manner that the front side of the crystal and the front electrode are freely accessible, and adapted to come into abutment with the flow cell element of the piezoelectric sensor arrangement, when the first and second parts of the piezoelectric sensor arrangement are moved from their open position to their closed position, whereby it sealingly covers the recess of the flow cell element, thus forming a flow cell together with the flow cell element.

The present invention also relates to a flow cell element which is provided with an outwardly open recess and inlet and outlet fluid channels by means of which a fluid sample can be lead through the recess, said recess being surrounded by an abutting surface, at least said abutting surface and the portion of the abutting part closest to the abutting surface being made of an elastic material, wherein said abutting part is adapted to come into abutment with the piezoelectric quartz crystal in the above mentioned sensor when the first and second parts of the piezoelectric sensor arrangement are moved from their open position to their closed position, whereby the recess is sealingly covered by the crystal, thus forming a flow cell together with the sensor element.

The present invention also relates to a flow cell comprising the above mentioned flow cell element, wherein the recess is covered by the crystal of the above mentioned sensor element.

BRIEF DESCRIPTION OF THE DRAWINGS

The invention will now be described in detail by reference to the accompanying drawings, in which:

FIG. 6b shows a cross section representation of the quartz crystal plate in FIG. 6a;

DESCRIPTION OF THE EMBODIMENTS

Figure 1:
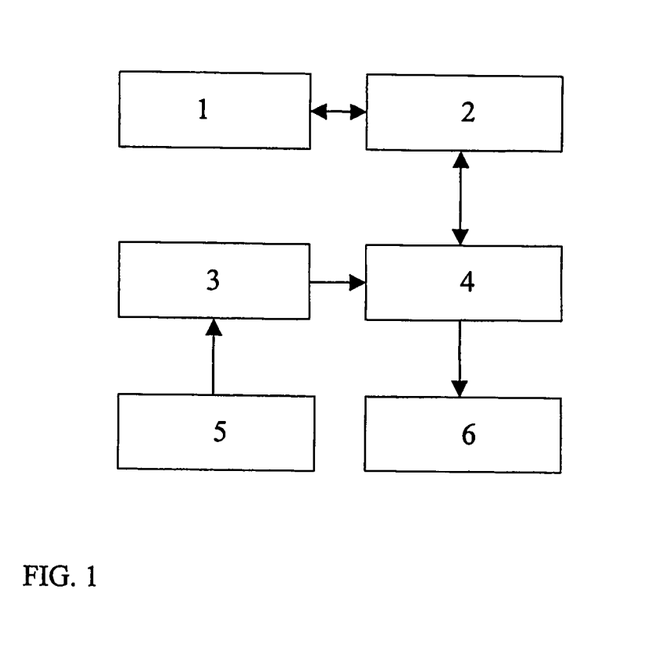
FIG. 1 shows a block diagram of a typical piezoelectric resonator analysis system.

The piezoelectric sensor arrangement of the present invention is intended to be a part of an analysis system, which is shown in FIG. 1, for sensing chemicals and chemical reactions in liquids. Such an analysis system comprises a computer (PC) 1 for controlling and presenting data, a frequency counter 2, a sample insertion unit 3, a sensor arrangement 4, a buffer solution container 5 and a waste container 6.

Figure 2A:
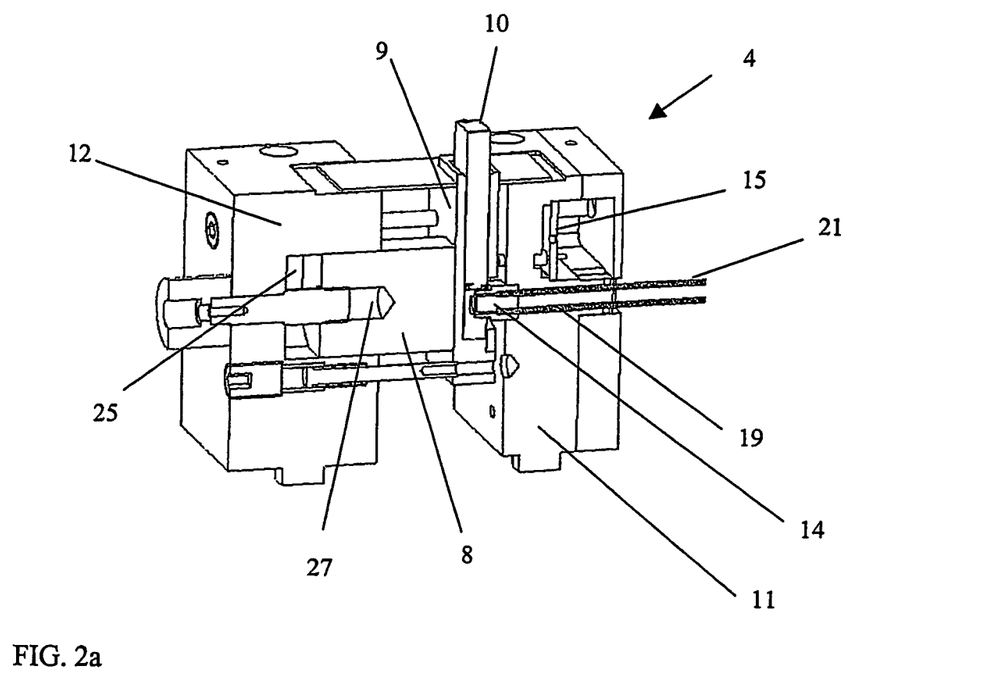
FIG. 2a shows an oblique view partly in cross section of a piezoelectric sensor arrangement according to a first preferred embodiment of the present invention in a closed position.
Figure 2B:
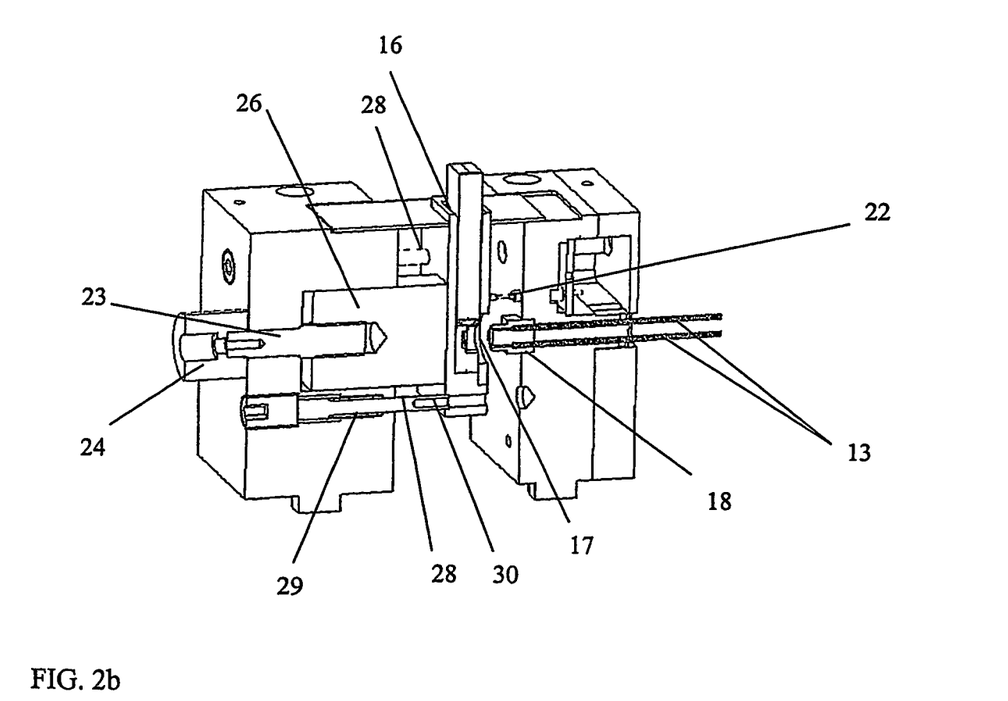
FIG. 2b shows a similar view as in FIG. 2a, but with the piezoelectric sensor arrangement in an open position.

FIGS. 2a and 2b show a piezoelectric sensor arrangement 4 according to a preferred embodiment of the invention. The arrangement comprises a docking system, which includes a first part 8 provided with means 9 for receiving a sensor element 10 and a second part 11, 12, which comprises fluid channels 13 for the sample and a flow cell element 14. The flow cell element is preferably removable. The first and second parts are movable in relation to each other between a closed position (FIG. 2a) and an open position (FIG. 2b). The sensor element 10 exposes a piezoelectric quartz crystal plate 32 (see FIG. 3) that is partially coated with electrode material on both sides. One of the electrodes is freely accessible and is intended to be exposed to the sample and the electrode material of this electrode will accordingly interact with the components of the sample. The other electrode functions as a counter electrode. The removable flow cell element 14, which is shown separately in FIG. 7, comprises a recess 45 and inlet and outlet fluid channels 46 for leading the sample fluid through the recess. The recess 45 is provided in an abutting part 43 of the flow cell element and is surrounded by an abutting surface 48. The part of the abutting part that includes the abutting surface and the portion closest to the abutting surface is made of an elastic material, which is elastic enough to seal against the piezoelectric quartz crystal without breaking it. The first part 8 and the second part 11, 12 of the sensor arrangement are arranged such that, when the first and second parts are moved from the open position to the closed position, the upper surface 48, which is the abutment surface of the abutment part 43 comes into abutment with the exposed piezoelectric quartz crystal 32 of the sensor element 10, whereby the recess 45 is sealingly covered by the piezoelectric quartz crystal 32 in the closed position, thus forming a flow cell by the flow cell element and the quartz crystal. The parts of the flow cell, i.e. the piezoelectric crystal and the abutting part 43 of the flow cell element, with its recess 43, are held together only by means of a pressing force, exerted by the first and second parts (8; 11, 12) of the sensor arrangement as will be described in further detail below, and thus no adhesives or mechanical fixing means are needed. The design of the flow cell element will be described in greater detail below.

The arrangement further includes a signal source 15, for transmitting electrical signals to the electrodes. The signal source and the electrodes form an electric circuit and the oscillation characteristics of the crystal plate 32 is monitored by a measuring device that is connected to the signal source, e.g. by measuring the changes in crystal resonance frequency.

The sensor element receiving means 9 has a cavity, which is externally accessible via a slot 16, and through which slot the sensor element 10 can be inserted. It is also provided with an opening 17 through which the crystal plate of the sensor element can come into contact with the flow cell element 14. In the bottom of receiving part 9 a drainage hole is preferably provided, to avoid flooding should a leakage occur.

The first part 8, i.e. the sensor receiving part, of the docking system of the sensor arrangement is preferably arranged as a movable part, slidably mounted to the second part 11, 12, which is then fixed. The sensor receiving 8 part can thus be slidably moved with relation to the second part 11, 12, between the open position and the closed position, in which the quartz crystal plate 32 comes into abutment with the flow cell element in the second part 11, 12. Alternatively, the second part 11, 12 may be arranged as a movable part, whereas the first part 11 is fixed.

The second part 11, 12 of the arrangement in its turn includes one sample providing part 11 and one operating part 12. The sample providing part has a recess 18 into which the flow cell element 14 is inserted. The recess is adapted so as to correspond to the dimensions of an insertion part 44 of the removable flow cell element 14 that is directed away from the sensor element. Preferably the dimensions of the recess 18 are slightly smaller than the insertion part 14 so that the flow cell element is retained by friction. The flow cell element may also be attached by screws or other mechanical means. The sample providing part has two through-bores 19 for conduction of the sample to and from the flow cell. The through-bores are externally accessible at one end and lead to the bottom of the recess 18 at their other end. Flow channel tubing 13 can advantageously be inserted into the through-bores and be arranged to extend out into the recess 18 so that the tubing is partially inserted into the flow channels 46 of the flow cell element 14. The sample is supplied to the flow channel by means of a pressure differential between the inlet and the outlet of the flow channels. The pressure differential can be achieved by a syringe or a pump. The flow channel tubing is made of a material that is inert to the sample, such as PEEK or stainless steel and has an internal diameter of 0.1-1 mm. The sample providing part is also provided with electrical contacts 22 for connection with electrical contact areas on the sensor element. The contacts are preferably spring loaded contacting pins, with a spring force of 10-200 g, preferably 25-75 g.

The operating part 12 includes an operating screw 23 which is connected to the sensor receiving part 8 by thread engagement and which is operated by a handle 24 that is fastened to the screw. The operating part 12 has a cavity 25, which fits a nut 26. The operating screw 23 is attached to the operating part 12 in such a manner that it can rotate without any axial motion with relation to the operating part. The threads of the screw engage internal threads of a bore 27 in the sensor element receiving part 8. Upon rotation of the screw 23 the sensor element receiving part 8 will thus move linearly towards or away from the sample providing part 11, depending on the rotational direction. The movement can be performed either manually or automatically with a motor and an electronic control system. It is important that the positioning of the piezoelectric crystal against the flow cell element is very accurate. In order to obtain a precise fitting in of the crystal plate, the sensor element receiving means 9 may be mounted on three guide rods 28, which are spring loaded by means of springs 29 and steered by slide bearings 30 in the operating part 12, guided between the closed and open positions by means of along a linear path. The threads of the screw 23 and the bore 27 have a very low pitch, which enables a very exact adjustment of the force with which the crystal plate is pressed against the flow cell element. The pressing force of the crystal plate on the flow cell element should be as low as possible, so as to avoid excessive dampening of the crystal plate, but must be high enough to sufficiently seal the flow cell, i.e. that no sample leakage occurs. The force is dependent on the material hardness of the material chosen for the flow cell element and can be determined experimentally by running the sensor arrangement with a test sample of the desired fluid intended for use in the analysis, e.g. water.

The operating part 12 of the sensor arrangement may preferably also be provided with a locking device that locks the screw as it reaches the position in which the crystal abuts the flow cell element with the empirically determined appropriate force. Such a device may consist of a spring-loaded locking pin on the nut 26 that enters a slot in the screw 23. As an alternative to the screw and nut, a hydraulic or pneumatic cylinder may be used for the movement of the sensor receiving part.

The sensor arrangement may be constructed as a multichannel system, having several flow cells, each of them formed by abutment of a crystal plate and a flow cell element. In one embodiment, the sensor arrangement includes one sensor element receiving means 9 per flow cell and corresponding flow cell elements for each sensor element. In another embodiment, a number of crystal plates may be provided on a single sensor element, each crystal plate having a corresponding flow cell element on the sample providing part. The flow cell element may also be shaped so as to comprise several flow cell recesses, each having separate inlet and outlet channels. The flow cells may be coupled in parallel or in series. If the flow cells are coupled in parallel, a number of parallel sensor runs may be performed simultaneously. The crystal plates of the different flow cells may have different specific coating, thereby giving an opportunity to detect different substances in the sample. This is particularly practical if the flow cells are coupled in series.

The sensor arrangement may optionally be provided with electromagnetic shielding and means for regulating the temperature.

Figure 3:
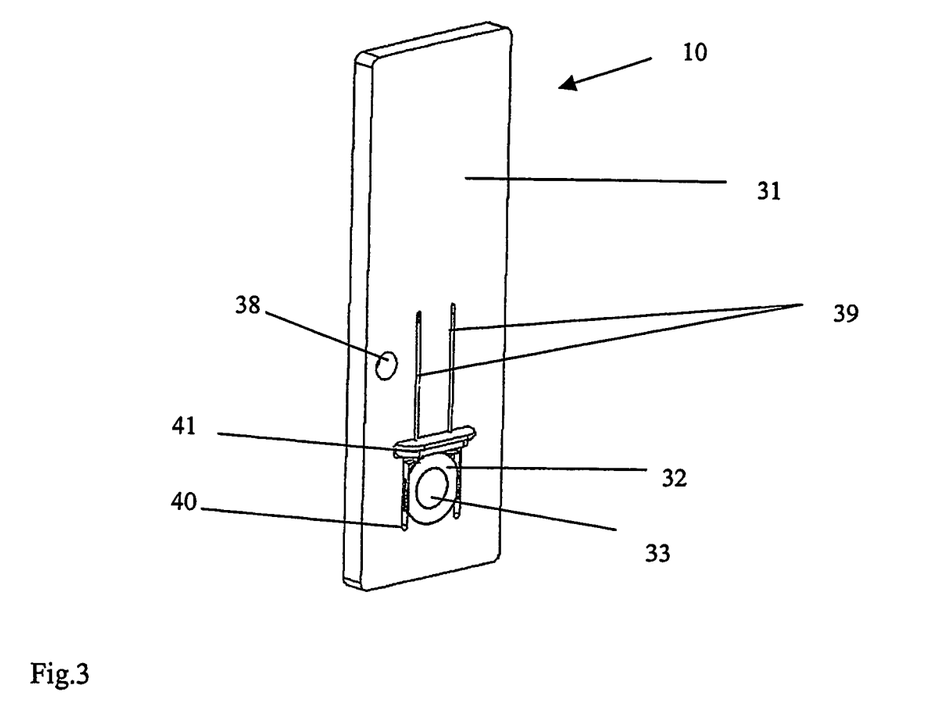
FIG. 3 shows an oblique view of a sensor element to be used in the arrangement in FIG. 2a,b according to one embodiment of the present invention.
Figure 4:
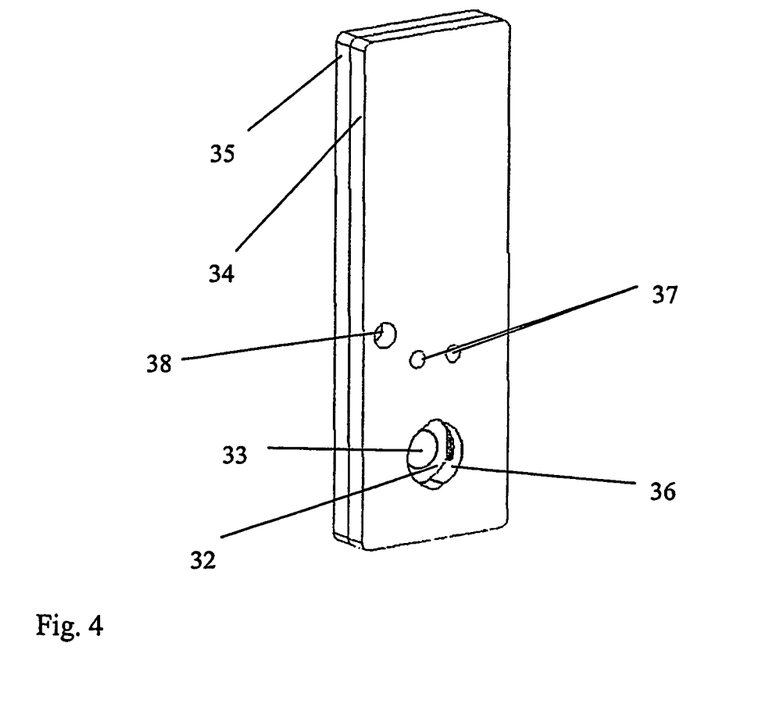
FIG. 4 shows an oblique view of an alternative embodiment of a sensor element to be used in the sensor arrangement.

A sensor element to be used in the sensor arrangement is shown in FIGS. 3 and 4. The sensor element comprises a carrier 31 to which a piezoelectric quartz crystal plate 32 is attached. The carrier has the shape of a plate and has a surface area of 1-100 cm$^2$, preferably 5-30 cm$^2$ and more preferably 10-20 cm$^2$. The thickness of the carrier is 0.5-10 mm. The crystal that is attached to the carrier is shown without the carrier in FIGS. 5 and 6, and has a front side 32 and a rear side (not shown). The front side 32 is intended to come into contact with the fluid sample and is provided with a front electrode 33 and the rear side is provided with a rear electrode, which functions as a counter electrode. The electrodes are preferably made of gold. Both electrodes are adapted to receive electric signals for generation of an oscillating motion of the crystal. The crystal is arranged on the carrier in such a manner that the front side of the crystal 32 and the front electrode 33 are freely accessible for contact with the sample, whereas the counter electrode is directed towards the carrier plate, such that it does not come in contact with the sample. In the embodiment shown in FIG. 3 the carrier consists of a single rectangular plate, which has a smooth surface that is substantially flat.

In another embodiment of the sensor element, shown in FIG. 4, the carrier comprises a front part 34 and a rear part 35, between which the crystal 32 is attached. Both parts have the same width and length and the front part is provided with an opening 36 for exposure of the crystal to the sample and is also provided with apertures, which expose electrical contacting areas 37 that are thus externally accessible for the electrical contacts 22 on the sample providing part.

Irrespective of its design the carrier comprises a recess or opening in the area of the rear electrode, so as to allow free oscillation of the crystal. If the carrier comprises an opening the electrodes may also be electrically contacted from the rear side of the crystal. The recess or opening is designed such that the carrier supports the periphery of the piezoelectric crystal from the rear side when it is pressed against the flow cell element. This supporting feature of the carrier further balances the sealing forces exerted by the flow cell element on the crystal plate, when it is subjected to the pressing forces of the abutment with the flow cell element. The carrier is preferably also provided with an aperture 38 for insertion of a locking pin, which is intended to ensure the correct position of the sensor element in the receiving means.

The surface area of each electrode 33 is smaller than the surface area of the crystal, preferably 10-90% of the crystal area. Thus each side of the crystal comprises an area between the electrode edge and the crystal periphery that is not covered by electrode material. In order to be able to obtain electrical contact between the electrode and the holding plates, a connecting portion 33a of the electrode extends towards the crystal periphery thus presenting a conductive but not oscillating extensions of the electrode.

Figure 5:
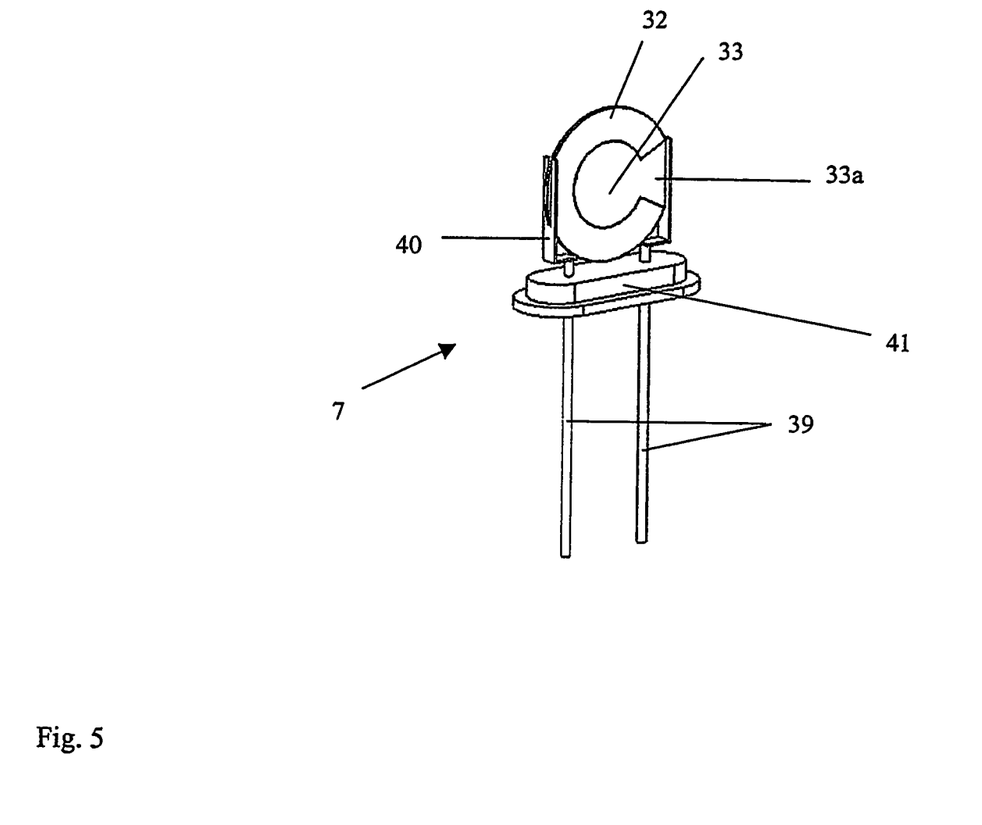
FIG. 5 shows an oblique view of a quartz crystal plate with a metal holder.

Both electrodes 33 are electrically connectable to external contacts 22, by their connection portions 33a. In the embodiment shown in FIG. 3, the crystal plate is held by a holder 7, which also provides electrical contact between the electrodes and the electrical contacts 22 on the sample providing part, via contacting legs 39. The crystal with the holder is also shown in FIG. 5. The holder comprises two metal holding plates 40, having an aperture into which the periphery of the crystal is inserted. In order to improve the electrical contact additionally, the holding plates may also be soldered to the electrodes. The holding plates are attached to a mounting plate 41 and electrically connected to the contacting legs 39. The holding plates 40 and their respective contacting leg 39 are preferably made in one piece. The holder 7 with the crystal is arranged on the carrier such that the contacting legs can be directly contacted by the electrical contacts 22 of the sample providing part. In this embodiment the carrier is provided with recesses that can partly receive the holder, so that the crystal is supported by the flat surface of the carrier plate. In the embodiment of the sensor element comprising a rear part 35 and a front part 34 shown in FIG. 4, both parts are provided with recesses for the holder. The apertures in the front part are located right in front of the contacting legs 39 so that the electrical contacts 22 of the sample providing part can come in contact with the contacting legs.

Figure 6A:
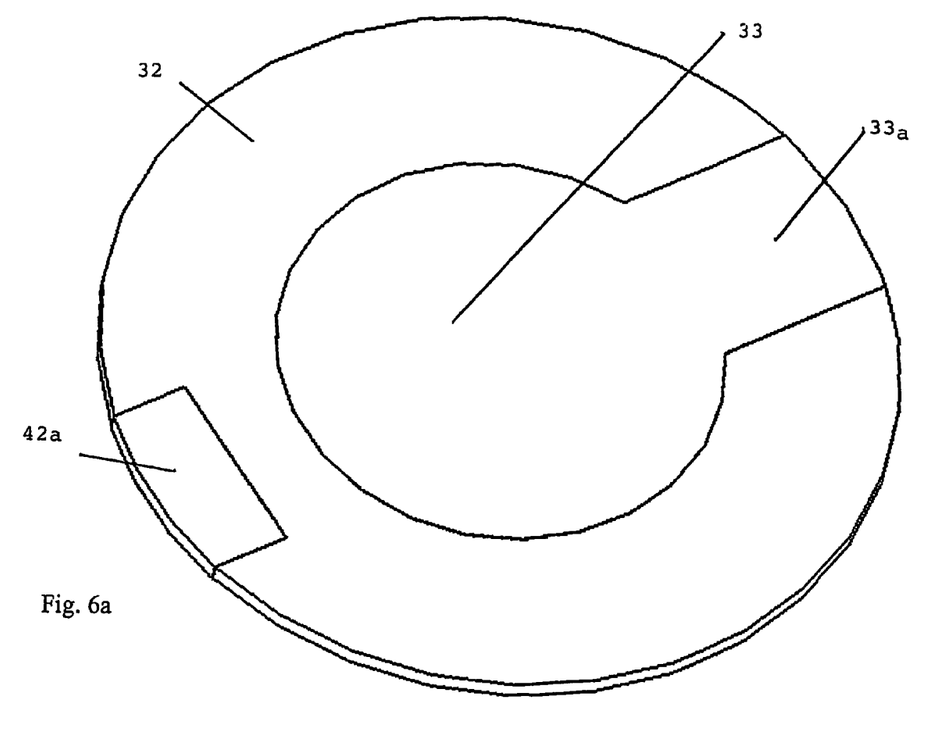
FIG. 6a shows an oblique view of a quartz crystal plate.
Figure 6B:
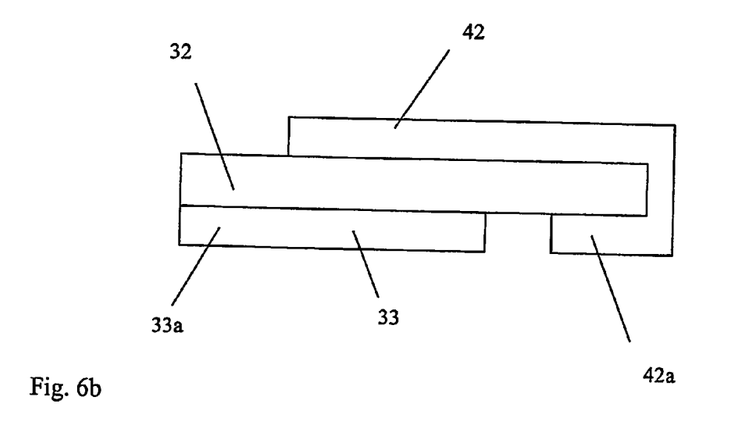

In another embodiment the crystal plate is attached directly to the carrier, i.e. no holder is used. The crystal plate is attached to the carrier e.g. by means of an adhesive if a single plate carrier is used. If a double plate carrier is used the crystal plate may be clamped between the rear and front parts of the carrier with additional use of adhesive attachment if desired. The adhesive does not impair the detection, since it has no sealing function and is applied to the side of the crystal plate that does not come in contact with the sample. The use of an adhesive or of clamping means in this embodiment of the present invention is thus not to compare with the use of adhesives or clamping that has the purpose to fix the crystal to the flow cell element means, which is disclosed in prior art. When a double plate carrier is used the contacting of the electrodes on the crystal surface is then performed by direct contact of the electrical contacts 22 of the sample providing part. This can be achieved by arranging the electrical contacts 22 such that they can reach the crystal surface by using spring-loaded contacting pins that can contact directly to the electrode surfaces, via the connecting portion 33a, with a limited force. Such spring-loaded contacting pins are commercially available. As the crystal has two electrodes, one on each side of the crystal, the electrodes may have a special design that enables direct contacting with contacting pins. One of the electrodes 42 is thus, as is shown in FIGS. 6a and 6b, designed so to include a portion 42a that extends to the periphery of the crystal, around the edge of the crystal plate and up on the other side of the crystal plate. By this design the contacting area 42a of one of the electrodes is situated on the opposite side of the crystal plate and on the same side as the other electrode 33. This makes it possible to contact both electrodes 33, 42 from one side of the crystal plate. The electrodes can be contacted electrically from the front side of the crystal plate, i.e. flow cell side, or from the rear side, i.e. the counter electrode side. Contacting the electrodes on the rear side has the advantage that there is more space available for the contacting pins on the non-fluid side of the crystal. In this case the carrier has an opening which exposes also the rear side of the crystal and the spring-loaded electrical contacts are provided on the operating part. The crystal will thus be docked from both sides.

The electrodes are, however, most advantageously contacted on the flow cell side of the crystal. This enables a less complicated construction of the sensor arrangement, since the crystal plate only has to be docked from the front side. The arrangement thus contains less movable parts. There is little space for the electrical contacts 22 to reach the contacting areas of the electrodes. In order to enable the electrical contacts 22 to reach both connecting portions 33a, 42a, also the electrical connecting portion 33a of the electrode on the flow cell side is designed so as to reach the periphery of the crystal and if desired also around the crystal edge. The spring-loaded electrical contact pins can then more easily be contacted with the conductive but not oscillating extensions of the electrodes on the periphery of the crystal.

In another embodiment that uses the crystal plate without a holder, the carrier has a printed conducting pattern that connects the electrodes to the electrical contacting areas 37.

The sensor arrangement of the present invention is particularly useful for detection of chemical substances and chemical interactions/reactions, especially in biochemical applications. The front electrode 33 on the front side of the crystal is then coated with an active substance that is specific to the substance or the reaction to be analysed. The surface coating can be applied on the electrode surface prior to the attachment of the crystal plate to the carrier, but may also be performed after the attachment, which may be advantageous in some applications.

The sensor element is preferably provided with a protective cover, such as a removable protective foil, that is arranged so as to cover the crystal and thus to protect the electrode surface from dirt and mechanical damage. The protective foil may be arranged such that it is peeled off as the sensor element is inserted into the receiving means. The protective foil is preferably resealable. As an alternative a sliding cover may be used, which is arranged such that is it shoved aside when the sensor element is inserted into the sensor element receiving means of the sensor arrangement in connection with an analysis run. The sliding cover is preferably arranged in the sensor element in connection with actuating resilient means, which forces the cover back to the closed position when the sensor element is removed from the sensor arrangement after analysis. This arrangement additionally protects the user from coming into contact with the sample, which is a particular advantage when the sensor arrangement is used for analysis of samples that might be infectious, e.g. blood samples.

Figure 7:
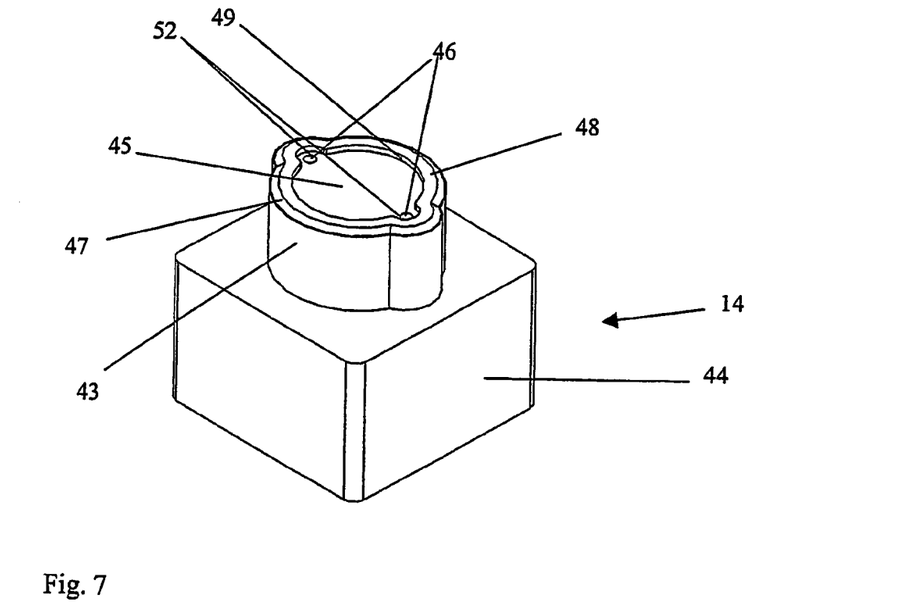
FIG. 7 shows an oblique view of a flow cell element of the present invention.

The flow cell element 14 comprises an abutting part 43 and an insertion part 44 on top of each other. The abutting part has the geometry of a cylinder, having a cross section that substantially corresponds to the geometry of the electrode 33. In the case a double plate carrier is used the cross section of the abutting part must be smaller than the opening 36 in the front part of the sensor element, so that the abutting part can be inserted into the opening 36 and thus reach the crystal plate. The insertion part 43 of the flow cell element is has also the geometry of a cylinder, the cross section of which has a shape that is adapted to the bottom of recess 18 in the sample providing part of the sensor arrangement. The cross section of the insertion part 43 and may be of any shape, as long as it corresponds to the recess 18. Preferably the cross section is such that the flow cell element only can be inserted into the recess such that the inlet and outlet channels 46 are placed just in front of the fluid channels 13. As has been described above, the insertion part should be slightly larger than the recess, so that the flow cell element may be retained by friction. The base of the insertion part may for example rectangular. The abutting part 43 and the insertion part 44 may be separate parts attached to each other, but are most advantageously made in one piece.

The abutting part 43 of the flow cell element 14 is provided with an outwardly open recess 45 and inlet and outlet fluid channels 46 by means of which a fluid sample can be lead through the recess. The recess 45 is surrounded by an abutting surface 48 and has a bottom that is a flat surface. In one embodiment of the present invention the surface 48 is constituted by a ridge 47 that has a smooth upper surface, i.e. the abutting surface 48. The depth of the recess 45, i.e. the height of the ridge is 0.01-0.5 mm, preferably 0.05-0.2 mm. The smooth upper surface 48 of the ridge has a width of 0.05-1 mm.

At least the abutting surface 48 and the portion of the abutting part that is closest to that surface is made of an elastic material. The thickness of the elastic material should be large enough to provide sufficient elasticity to the abutting surface, in order to seal the flow cell element effectively against the crystal surface, without breaking or otherwise damaging the crystal. The thickness of the elastic portion of the abutting part required to obtain a satisfying result is dependent on the choice of elastic material, and is typically at least 100 nm. Preferably at least the ridge 47 of the flow cell element is made of elastic material, but even more preferably the whole flow cell element is made in one piece of elastic material, since this simplifies the manufacture of the flow cell element.

As mentioned above the choice of material for the flow cell element, or at least the abutting surface, with respect of its elasticity is very important for the performance of the piezo-electric sensor arrangement. A too stiff material may break the crystal or cause leakage of the flow cell created. A material that is too soft may cause irreproducible flow cell geometries, due to insufficient mechanical stability in the elastic material, and may dampen the crystal oscillation excessively. When making the choice of elastic material for the flow cell element a number of factors have to be taken into account. Firstly, the surface roughness of the crystal surface 32 affects the elasticity required to efficiently seal the flow cell, as well as the surface roughness of the abutting surface 48. Rougher surfaces require a more elastic material. Secondly, the chemical surface properties of the flow cell, i.e. the chemical surface properties of the crystal surface, the chemical properties of the fluid used in the system and the elastic material itself, have an influence on the choice of elastic material element. For instance, a polar fluid, such as water, may be easily contained in the flow cell if the surfaces of the flow cell element and the crystal are hydrophobic. This means that in such a case a less elastic material may be used, without risking leakage. Thirdly, the pressure drop throughout the system also influences the elasticity needed, i.e. a high pressure drop requires a better sealed flow cell, which means that a higher pressure drop needs a more elastic material. Suitable elastic materials are e.g. PUR, Silicon or PDMS etc.

The optimal hardness, i.e. the optimal elasticity, of the flow cell element is thus difficult to dependent on the properties of the system. In most cases the elastic material should have a hardness of 10-95° Shore, preferably between 45-95° Shore. The elasticity range between 45 and 55° Shore for the elastic material of the flow cell element creates the most robust system. Choosing the elasticity within that range will create a system that can accept many different types of fluids and surface properties of the crystal and flow cell element. The system will also be able to handle different pressure drops throughout the system as well as relatively rough surfaces on crystal and flow cell elements.

In use, the abutting surface of the flow cell element will abut to the surface of the crystal plate of the sensor element so that the crystal plate covers the recess, whereby a flow cell is formed. The ridge 47 should have a shape that corresponds to the shape of the electrode 33, intended for use as the sensor electrode. The recess should be slightly larger than the electrode surface. For instance, in the case of a circular electrode, the ridge should also have a substantially circular shape and the circle formed by the inner edge 49 should have a radius of the electrode plus x, where x is 0-1 mm, preferably in the range 0.1-0.5 mm. To stabilize a thin dimension of the ridge and to minimize the contact area with the crystal surface, the ridge can be given a tapered shape, providing a wider base and a narrower surface 48.

At the bottom of the recess, inlet and outlet fluid channels 46 are arranged close to the periphery of the recess and diametrically opposed to each other, so that the sample flow enters the flow cell at the periphery of the electrode, in order to avoid any pulsation on the electrode. In one embodiment the recess has extensions 52 in which the inlet and outlet fluid channels 46 are arranged. By this arrangement the sample may enter the flow cell outside the electrode surface of the crystal, flow over the electrode surface and exit the flow cell outside the electrode surface. The ridge can thus abut to the surface of the crystal very close to the edge of the electrode. This results in much better flow characteristics in the flow cell.

Figure 8:
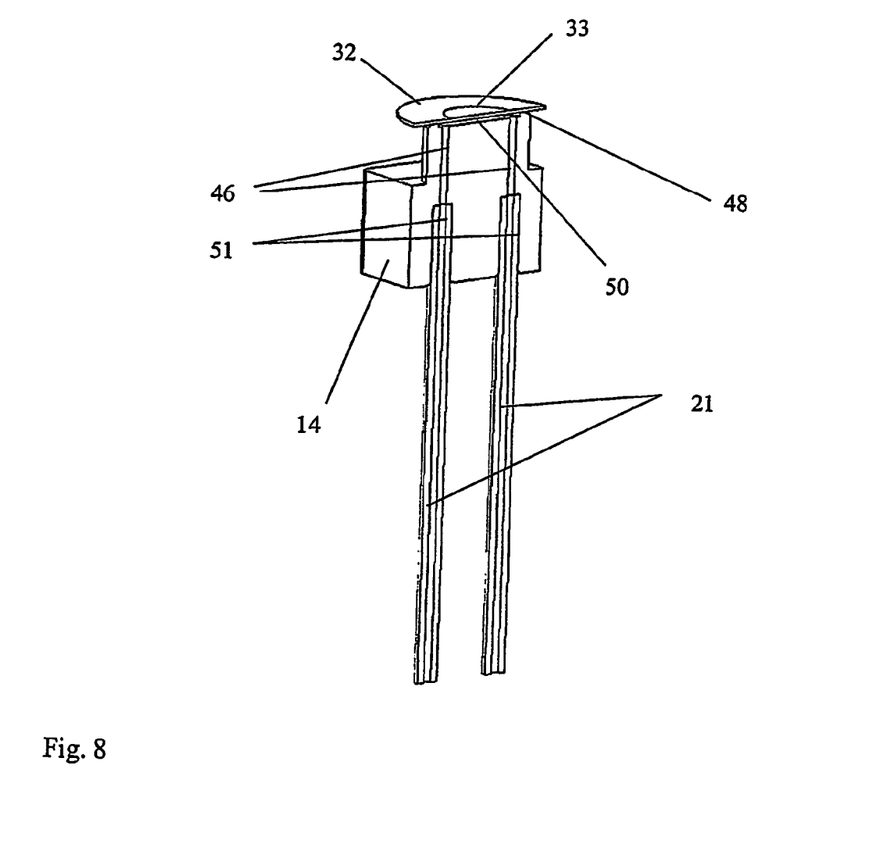
FIG. 8 shows a cross section representation of a flow cell of the present invention.

As shown in FIG. 8, the flow channels 46 run through the flow cell element from the side of the flow cell element that is to be inserted into the recess 18 in the sample providing part of the sensor arrangement to the recess 45 that will form the flow cell 50. The sample will be supplied to one of the flow channels 46 and emptied through the other after having passed the flow cell. The flow channels have a larger diameter at the end that is directed away from the flow cell, than at the end closest to the flow cell. Cylindrical cavities are thus provided, which are adapted to receive and enclose the ends 51 of the sample supply tubing 21. Preferably these cylindrical cavities have a diameter slightly smaller than that of the sample supply tubing to accomplish a squeeze-fit joint, with zero dead volume. Consequently, fluidic connections are achieved that have zero dead volume and, in addition, causes minimal fluidic distortion to the flow, decreasing the dispersion and thus achieving higher quality in the analysis.

In operation of the sensor arrangement, it is in its open position at the beginning of an analysis procedure. A sensor element 10, 40 is inserted into the sensor element receiving means 9. A sensor element is chosen, which has a coating on its sensing electrode that is specific to the substance or reaction to be detected or analysed. The sensor receiving part 8 is then moved by means of the screw 23 towards the sample providing part 11 until the crystal plate of the sensor element abuts the flow cell element and the contacting areas of the sensor element 37 come in contact with contacting pins 22. A flow cell 50 has now been formed and electrical contact with the sensor electrodes and the measuring equipment has been established. A sample is supplied to the flow cell via the flow channel tubing 21 and one of the flow channels 46. As the sample passes through the flow cell the component to be detected interacts or reacts with the coating of the sensor electrode surface, whereby the resonance frequency of the electrode changes. The measuring equipment registers the change in resonance frequency. As the analysis is completed, the sensor receiving part 8 is moved away from the sample providing part 11 into the open position and the used sensor element is removed. The sensor arrangement is now ready for use with a new sensor element. In some analyses the fluid channels and the reusable flow cell element 14 is rinsed off, e.g. by leading water or any other suitable cleaning medium through the flow cell. When desired, the flow cell element 14 may be removed and exchanged.

The invention claimed is:

1. A piezoelectric sensor arrangement for analysis of at least one liquid sample, comprising:
   a signal source;
   a measuring device; and
   a docking system comprising a first part and a second part, wherein
   said first part comprises means for receiving a sensor element which sensor element comprises a piezoelectric quartz crystal having a freely accessible electrode and which electrode is positioned to contact the liquid sample when in use, said means for receiving comprising an opening allowing said sensor element to contact a flow cell element when in use;
   said second part comprises liquid sample channels to conduct the sample and a flow cell element;
   said flow cell element comprises an abutting part provided with an outwardly open recess surrounded by an abutting surface, inlet liquid sample channels, and outlet liquid sample channels;

said inlet fluid channels and said outlet liquid sample channels are configured to lead the liquid sample through said recess;

said abutting surface and a portion of said abutting part closest to said abutting surface are made of an elastic material;

said elastic material is capable of forming a seal against the surface of the piezoelectric quartz crystal;

said first and second part are movable in relation to each other between a closed position and an open position;

when said first and second parts are moved from said open position to said closed position an upper surface of said abutting part of said flow cell element comes into abutment with said piezoelectric quartz crystal; and when said first and second parts are in said closed position a seal forms between said piezoelectric quartz crystal and said recess of said flow cell element to create a flow cell.

2. A sensor arrangement according to claim 1, wherein the flow cell element is removable.

3. A sensor arrangement according to claim 1, wherein said elastic material has a hardness of 10-95° Shore.

4. A sensor arrangement according to claim 3, wherein said elastic material has a hardness of 45-95° Shore.

5. A sensor arrangement according to claim 1, wherein the first part is arranged to move slidably with relation to the second part, so that the quartz crystal comes into abutment with the flow cell element in the second part.

6. A sensor arrangement according to claim 1, wherein the first part is guided between said closed and open positions by means of guide rods.

7. A sensor arrangement according to claim 1, wherein the first part is guided along a linear path.

8. A sensor arrangement according to claim 1, wherein the means for receiving the sensor element has a cavity provided with a slot, through which the sensor element can be inserted and an opening through which the crystal of the sensor element can come into contact with the flow cell element.

9. A sensor arrangement according to claim 1, wherein the second part comprises a sample providing part that has a recess in which the flow cell element is arranged and an operating part that includes means for movement of said first part.

10. A sensor arrangement according to claim 9, wherein the means for movement of said first part includes a screw which is connected by thread engagement to the first part and which is operated by a handle.

11. A sensor arrangement according to claim 1, wherein the second part is provided with electrical contacts for connection with electrical contact areas on the sensor element.

12. A sensor arrangement according to claim 11, wherein the electrical contacts are spring loaded contacting pins.

13. A sensor arrangement according to claim 11, wherein the electrical contacts are arranged on a sample providing part.

14. A sensor arrangement according to claim 1, wherein the recess of the flow cell element has a shape that corresponds to the shape of the first electrode.

15. A flow cell element for use in the piezoelectric sensor arrangement of claim 1, comprising: an abutting part comprising an outwardly open recess, inlet liquid sample channels, and outlet liquid sample channels, wherein said inlet liquid sample channels and said outlet liquid sample channels lead the liquid sample through said recess;

said recess is surrounded by an abutting surface;

said abutting surface and a portion of the abutting part closest to the abutting surface is made of an elastic material;

said abutting surface is adapted to come into direct abutment with the surface of the piezoelectric quartz crystal in a sensor element, so as to form a flow cell together with the sensor element, by being sealingly covered by the crystal, when the first and second parts of the piezoelectric sensor arrangement are moved from an open position to a closed position, wherein the inlet and outlet liquid sample channels are arranged closer to the periphery of the recess than to the center of the recess and diametrically opposed to each other, wherein the abutting surface that surrounds the recess comprises a ridge having a smooth upper surface; the recess has a bottom, and said bottom of the recess is a flat surface, and wherein the flow cell element is formed from one piece of elastic material.

16. A flow cell element according to claim 15, wherein said elastic material has a hardness of 10-95° Shore.

17. A flow cell element according to claim 16, wherein said elastic material has a hardness of 45-95° Shore.

18. A flow cell element according to claim 15, wherein the ridge has a width of 0.05-1 mm.

19. A flow cell element according to claim 15, wherein the recess has a depth of 0.01-0.5 mm.

20. A flow cell element according to claim 15, wherein the elastic material is selected from the group consisting of polyurethane, silicone and PDMS.

21. A flow cell element according to claim 15, wherein the recess has a depth of 0.05-0.2 mm.

22. A flow cell element according to claim 15, wherein the recess has extensions in which the inlet and outlet liquid sample channels are arranged.

23. A flow cell element for use in the piezoelectric sensor arrangement of claim 1, comprising: an abutting part comprising an outwardly open recess, inlet liquid sample channels, and outlet liquid sample channels, wherein said inlet liquid sample channels and said outlet liquid sample channels lead the liquid sample through said recess;

said recess is surrounded by an abutting surface;

said abutting surface and a portion of the abutting part closest to the abutting surface is made of an elastic material;

said abutting surface is adapted to come into direct abutment with the surface of the piezoelectric quartz crystal in a sensor element, so as to form a flow cell together with the sensor element, by being sealingly covered by the crystal, when the first and second parts of the piezoelectric sensor arrangement are moved from an open position to a closed position, wherein the abutting surface is constituted by a ridge that has a smooth upper surface, the inner edge of the ridge forming the periphery of the recess, wherein the recess has a bottom, and said bottom is a flat surface, and wherein the flow cell element is formed from one piece of elastic material.

* * * * *

UNITED STATES PATENT AND TRADEMARK OFFICE
CERTIFICATE OF CORRECTION

PATENT NO. : 8,591,812 B2  Page 1 of 1
APPLICATION NO. : 10/539065
DATED : November 26, 2013
INVENTOR(S) : Aastrup et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1967 days.

Signed and Sealed this
Twenty-second Day of September, 2015

Michelle K. Lee
*Director of the United States Patent and Trademark Office*